US00PP11845P2

(12) United States Plant Patent
Jessel, Jr.

(10) Patent No.: US PP11,845 P2
(45) Date of Patent: Apr. 24, 2001

(54) CARNATION PLANT NAMED 'CFPC HARMONY'

(75) Inventor: Walter H. Jessel, Jr., Gonzales, CA (US)

(73) Assignee: California Florida Plant Co LP, Salinas, CA (US)

( * ) Notice: Subject to any disclaimer, the term of this patent is extended or adjusted under 35 U.S.C. 154(b) by 0 days.

(21) Appl. No.: 09/181,277

(22) Filed: Oct. 28, 1998

(51) Int. Cl.[7] ..... A01H 5/00
(52) U.S. Cl. ..... Plt./273
(58) Field of Search ..... Plt./273, 276, 282, Plt./281, 277, 274

*Primary Examiner*—Bruce R. Campell
*Assistant Examiner*—Michelle Kizilkaya
(74) *Attorney, Agent, or Firm*—Christie, Parker & Hale, LLP

(57) ABSTRACT

A new variety of carnation plant producing white flowers with pink markings.

1 Drawing Sheet

BACKGROUND OF THE INVENTION

The present invention relates to a new and distinct variety of carnation plant which was discovered by me as a naturally whole branch mutation in a controlled planting of 'CFPC Passion' (U.S. Plant Pat. No. 10,416). The varietal denomination of the new variety is 'CFPC Harmony'.

SUMMARY OF THE INVENTION

Among the novel characteristics possessed by the new variety which distinguishes it is white flowers with very faint medium pink markings. When grown under glass in Salinas, Calif., in 4½ inch plastic pots plants are about 7¾ inches tall and about 7 inches diameter. Flower diameter averages about 1 9/16 inches with a crown of about ¾ inches (average). Foliage is about 3½ inches long and about 5/16 inches wide. The new variety is grown mainly under greenhouse conditions but can be transplanted into a garden environment or patio container outdoors protected from the direct sun, such as plantings by walls or near shaded areas. It is believed that with regular watering and feeding, new blooms will form and finish all year round.

Asexual reproduction by propagation by cuttings of the new variety as performed in Salinas, Calif., shows that the foregoing and other distinguishing characteristics come true to form and are established and transmitted through succeeding propagations.

COMPARISON WITH PARENT

The new variety differs from its parent in flower color.

BRIEF DESCRIPTION OF ILLUSTRATION

The accompanying illustration shows typical specimens of the vegetative growth and flowers of the new variety depicted in color as nearly true as it is reasonably possible to make the same in color illustration of this character.

DESCRIPTION OF THE NEW VARIETY

The following is a detailed description of my new variety, with color terminology in accordance with The Royal Horticultural Society Color Chart (R.H.S.C.C.). The terminology used in color description herein refers to plate numbers in the aforementioned color chart. Phenotypical expression may vary depending upon varying environmental, seasonal and cultural conditions.

The information provided herein is based on observations of plants grown inside commercial greenhouses at Salinas, Calif. The height of plant and flower and foliage size are established as an average using standard commercial cultural practices.

Classification:
- *Botanical.*—*Dianthus caryophyllus.*
- *Commercial.*—Carnation, greenhouse type, suitable for production as a pot spray.

1. Plant:
   - *Height.*—About 7¾ inches.
   - *Growing habit.*—Herbaceous, semi-upright.
   - *Blooming habit.*—As a spray (pot), about 2 to 3 blooms per spray.
   - *Blooming season.*—Year round.
   - *Breaking action.*—Good, about 10–11 laterals per plant, pinching is required.
   - *Rooting time.*—About 17 days.
   - *Disease resistance.*—Good, typical of carnations.
2. Foliage:
   - *Color.*—Upper side: Near 137A. Lower side: Near 137B.
   - *Size.*—About 3½ inches long, about 5/16 inches wide.
   - *Quantity.*—Numerous.
   - *Shape.*—Lanceolate.
   - *Texture.*—Smooth.
   - *Ribs.*—Central, Keeled.
   - *Arrangement.*—Bi-lateral along stem.
   - *Stem color.*—Near 135B.
   - *Pedicel.*—Near 135B.
   - *Lastingness.*—About 1 week after cutting.
3. Bud:
   - *Shape.*—Ovoid.
   - *Color.*—Near 138B.
   - *Length.*—About 1 3/16 inches.
   - *Diameter.*—About 7/16 inch.
4. Calyx:
   - *Number of bracts.*—About 5.
   - *Length.*—About ¼ inch.
   - *Width.*—About 3/16 inch.

*Color.*—Outside — near 138B. Inside — near 145C.
*Bursting/Splitting.*—Has not been observed.

5. Bloom:
*Shape.*—Round.
*Size.*—Diameter average: About 1 9/16 inches. Depth average: About ¾ inch.
*Color.*—General tonality: White with pink markings. At Maturity: Upper side: Whiter than 155D, near 68B pink markings. Lower side: Whiter than 155D, near 68B pink markings. Center: Whiter than 155D, near 68B pink markings. Outer petals: Whiter than 155D, near 68B pink markings.
*Keeping quality.*—Good.
*Fragrance.*—None to slight.

6. Petals:
*Number.*—About 15.
*Outer petals.*—Length: About 1⅔ inches. Width: About 9/16 inch.
*Central petals.*—Length: About 1⅓ inches. Width: About ¾ inch.
*Texture.*—Smooth.
*Form.*—Fan shaped.
*Appearance.*—Shiny.
*Margin.*—Smooth.

7. Reproductive organs:
*Stamens.*—None.
*Pistil.*—Number 1. Color: Whiter than 155D. Length: About 1 inch.
*Stigma.*—Number: About 3. Color: Whiter than 155D.
*Ovary.*—Shape: Conical. Color: Base — near 11D. Body — near 144A. Apex — near 144A.
*Fertility.*—Female: Very good. Male: None.

I claim:

1. A new and distinct carnation plant of the variety substantially as shown and described.

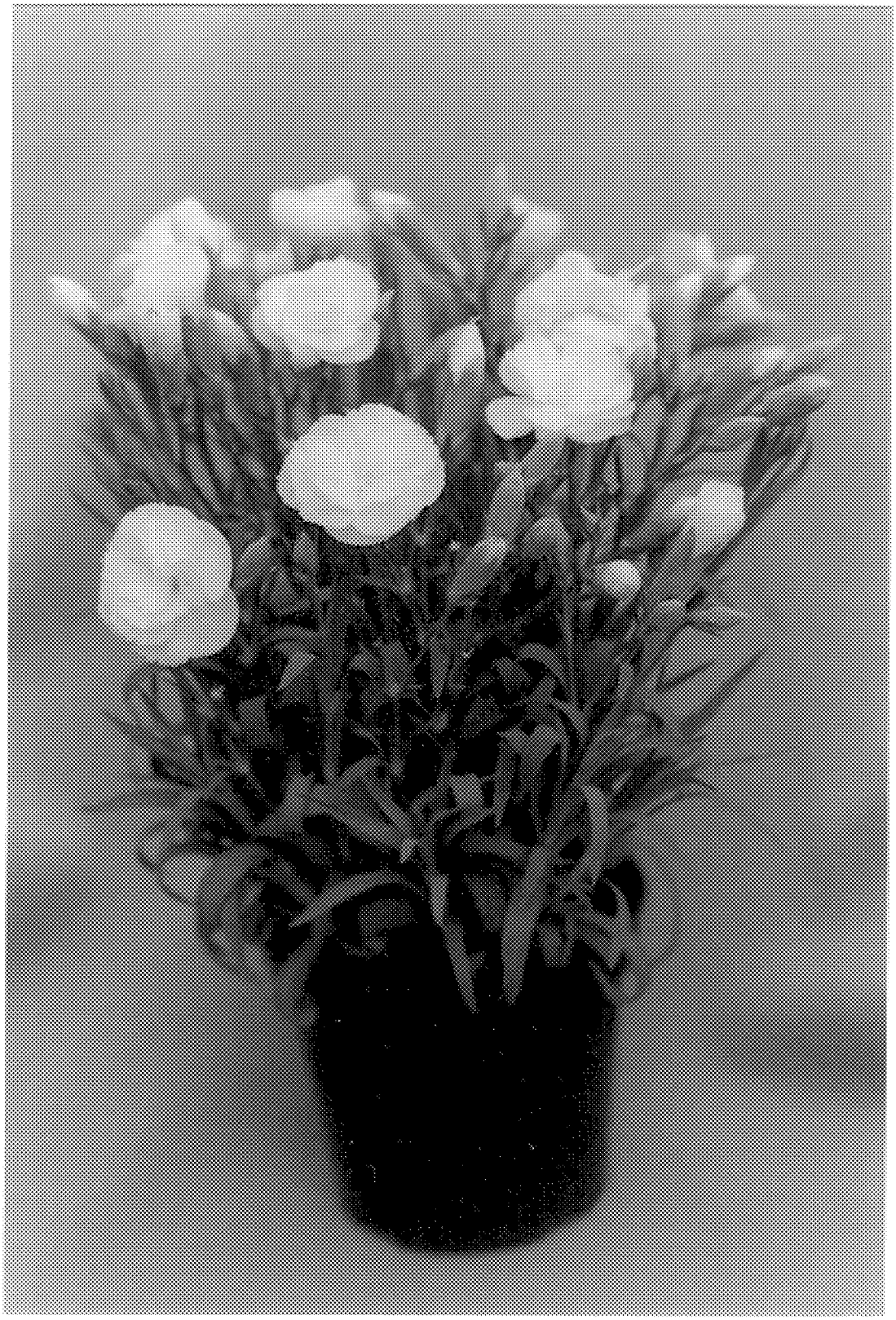

* * * * *